(12) United States Patent
Ludgate

(10) Patent No.: US 6,984,520 B1
(45) Date of Patent: Jan. 10, 2006

(54) BIOASSAY FOR THYROID STIMULATING ANTIBODIES

(75) Inventor: Marian Elizabeth Ludgate, Cardiff (GB)

(73) Assignee: University of Wales College of Medicine, Cardiff (GB)

( * ) Notice: Subject to any disclaimer, the term of this patent is extended or adjusted under 35 U.S.C. 154(b) by 0 days.

(21) Appl. No.: 09/509,687

(22) PCT Filed: Sep. 29, 1998

(86) PCT No.: PCT/GB98/02904

§ 371 (c)(1),
(2), (4) Date: Apr. 19, 1999

(87) PCT Pub. No.: WO99/16902

PCT Pub. Date: Apr. 8, 1999

(30) Foreign Application Priority Data

Sep. 30, 1997 (GB) .................................... 9720693

(51) Int. Cl.
*C12N 5/06* (2006.01)
(52) U.S. Cl. ...................................... 435/361; 435/325
(58) Field of Classification Search ................. 435/71, 435/361, 325; 436/506, 507
See application file for complete search history.

(56) References Cited

PUBLICATIONS

V. Krishna et al., "Repression of the Human Glycoprotein Hormone α-Subunit Gene by Glucocorticoids: Evidence for Receptor Interactions with Limiting Transcriptional Activators", *Mol. Endocrinology*, vol. 5, No. 1, Jan. 1991, pp. 100-110.

Himmler et al., "Functional Testing of Human Dopamine $D_1$ and $D_5$ Receptors Expressed in Stable cAMP-Responsive Luciferase Reporter Cell Lines", *Journal of Receiptor Research*, vol. 13, No. 1/04, Jan. 1993, pp. 79-94.

M. Ludgate et al., "Use of the recombinant human thyrotropin receptor (TSH-R) expressed in mammalian cell lines to assay TSH-R autoantibodies", *Molecular and Cellular Endocrinology*, vol. 73, Jan. 1990, pp. R13-R18.

L. Persani et al., "Measurement of cAMP accumulation in Chinese hamster ovary cells transfected with the recombinant human TSH receptor (CHO-R): a new bioassay for human thyrotropin", *J. Endocrinol. Invest.*, vol. 16, Jul. 1993, pp. 511-519.

F. Libert et al., "Cloning, Sequencing and Expression of the Human Thyrotropin (TSH) Receptor Evidence for Binding of Autoantibodies", *Biochemical and Biophysical Research Communications*, vol. 165, No. 3, Dec. 1989, pp. 1250-1255.

P.F. Watson et al., "A new chemiluminescent assay for the rapid detection of thyroid stimulating antibodies in Graves' disease", *Clin. Endocrinology*, vol. 49, Nov. 1998, pp. 577-581.

*Primary Examiner*—Patrick J. Nolan
(74) *Attorney, Agent, or Firm*—Young & Thompson

(57) ABSTRACT

An assay method for TSH-R autoantibodies or TSH comprises contacting a test sample, in the presence or absence of TSH, with cells from a clone expressing human TSH-R transfected with a reporter construct comprising cDNA of both (i) a reactant, such as an enzyme, capable of causing a measurable response when brought into contact with a corresponding substrate, such as a protein, and (ii) a promoter containing cyclic AMP (cAMP) response elements (CREs), whereby cAMP levels vary with expression of the reactant. Also disclosed are related kits, reporter constructs and related biological material.

3 Claims, No Drawings

BIOASSAY FOR THYROID STIMULATING ANTIBODIES

The present invention relates to an assay for measuring antibodies to the thyrotropin receptor; to an assay kit therefor; and specifically to the use therein of a cell line transfected with a-luciferase cDNA.

The thyrotropin receptor (hereinafter 'TSH-R') is known to regulate both the function and proliferation of the thyroid cell, and is stimulated by the hormone thyrotropin (TSH). The TSH-R is also a target for autoantibodies, which inhibit the binding of TSH to the receptor. These autoantibodies either block the action of TSH (TBAb) (i.e. TSH antagonists, which act as hypostimulants or inhibitors) or stimulate (hyperstimulate) the thyroid (TSAb) by acting as agonists to TSH.

Stimulation by TSAb is believed to be a mechanism operating in Graves' disease (GD), whilst inhibition by TBAb is believed to be the case in idiopathic myxoedema. Patients with hyperthyroid Graves' disease produce antibodies which mimic the action of TSH, leading to chronic stimulation of adenylate cydase; and whereas the autoantibodies in some patients with idiopathic myxoedema are also able to bind to the TSH-R, nevertheless this does not result in an increase in intracellular cyclic adenosine 3',5'-monophosphate (cAMP).

Many assays have been developed to measure TSH-R autoantibodies. The most widely used is a radioreceptor assay in which the binding of bovine $^{125}$I-TSH to detergent-solubilised porcine TSH-R is inhibited by immunoglobulins or sera from patients suspected of having TSH-R autoantibodies. The main problems with this assay are that it uses a non-human antigen; and that it measures binding and not biological activity, hence it is not able to distinguish between TSAb and TBAb.

It is clearly desirable to be able to distinguish between stimulation and inhibition, and therefore attempts have been made to develop a bioassay in which an effect of TSH (or its inhibition by TBAb) or TSAb is measured, such as the increase in CAMP. This may be done in thyroid slices or thyroid cells in culture and th greatest sensitivity, defined as the highest percentage of Graves' patients being positive, is achieved when the assay is performed in hypotonic (sodium chloride-free) medium. Both the radioreceptor and the bioassays are hampered by limited availability of biological material. To overcome this, a rat thyroid cell line (FRTL-5) has been developed, but here species differences may still be problematic. The recent cloning and sequencing of the TSH-R give unlimited access to recombinant human TSH—R.

As described by Libert et al in Biochem. & Phys. Res. Comm. 165 (3) 1250–1255 (1989) [all references herein are herein incorporated in their entirety, together with any cross-references therein], previous cloning of the dog thyrotropin receptor opened the way to molecular characterisation of the human TSH-R via isolation of human TSH-R cDNA clones; the analysis of the primary structure of the encoded polypeptide; and evidence that the recombinant molecule binds auto-antibodies found in patients with Graves' disease and idiopathic myxoedema. The dog TSH-R cDNA (a 2.8 kb fragment) was used to hybridise a human thyroid DNA library. Sequencing of the resulting clones gave rise to a 2292 nucleotide residue open reading frame encoding a 744 amino acid polypeptide having 90.3% similarity with the dog TSH-R. Transfection of the coding sequence in the pSVL vector of COS-7 cells allowed confirmation of the protein's ability to bind specifically TSH.

The co-transfection of Chinese hamster ovary (CHO) cells with a pSVL vector containing the coding region of human TSH-R led to the selection of cell lines particularly responsive to TSH or TSAb in terms of their CAMP accumulation (reported by Perret et al in Biochem. & Biophys. Res. Comm. 171 (3) 1044–1050 (1990)). Dose response curves of TSH-mediated CAMP accumulation were reported for clones JP14, JP26 and JP28, and the number of receptors per cell were found to be highest in clones JP14 and JP09.

This work gave rise to the possibility of a bioassay in which CAMP production is measured in CHO cells stably transfected with the human TSH-R in the presence of an autoantibody either alone (TSAb) or in the presence of TSH (TBAb), (Ludgate et al in Molec. & Cell. Endocrin. 73 R13–R18). However, such an assay is not sufficiently robust for routine use since it takes several days to perform, especially in view of the final detection of the generated CAMP by RIA, and requires tissue culture facilities.

Accordingly, the present invention provides an assay method for TSH—R autoantibodies or TSH comprising step:

(a) contacting a test sample, in the presence or absence of TSH, with cells from a clone expressing human TSH-R transfected with a reporter construct comprising cDNA of both a reactant, such as an enzyme, capable of causing a measurable response when brought into contact with a corresponding substrate, such as a protein, and a promoter containing cyclic AMP (CAMP) response elements (CREs), whereby CAMP levels vary with expression of the reactant.

Preferably, the assay method further comprises step:

(b) adding the corresponding substrate to cells thus contacted.

More preferably, the assay method still further comprises steps:

(c) measuring the response in the cells exposed to the substrate; and (d) comparing the response from test step (c) with the response from a standard or normal sample which has undergone steps (a) to (c).

The present invention therefore especially provides an assay, for TSH—R auto-antibodies or TSH, comprising:

(a) bringing into contact a test sample with cells from a clone expressing human TSH-R stably transfected with a reporter construct comprising cDNA of both a reactant capable of causing a measurable response when brought into contact with a corresponding substrate and a promoter containing CAMP response elements whreby CAMP levels vary with expression of the reactant;

(b) adding the corresponding substrate to cells thus contacted;

(c) measuring the response in the cells exposed to substrate; and (d) comparing the response from test step (c) with the response from a standard or normal sample which has undergone steps (a) to (c).

In the assay method of the present invention, all reagents used therein may be brought together in one or more steps, such as steps (a) to (d) defined herein. The notation of the steps (a) to (d) is not to be construed as meaning only that each step is carried out sequentially or that each component in the assay must be brought into individual contact with each other. For example, two or more of the steps (a) to (d) may be carried out substantially simultaneously; and/or all reagents used therein may be brought together in one step.

The assay method or any combination of the steps therein may be carried out by manual, partly automated or fully automated means.

Suitable reporter constructs (referred to in step (a)) are those in which the enzyme activity results in a colour change, fluorescence change or emission of light. Examples of such enzymes include chloramphenicol acetyl transferase (CAT), Firefly luciferase, Renilla luciferase, β-galactosidase, alkaline phosphatase, horseradish peroxidase or green fluorescent protein.

The cyclic AMP response element (CRE) of the reporter gene could be any promoter sequence or synthetic oligonucleotide which contains the CRE consensus sequence, TGACGTCA, preferably as a number of tandem repeats. A suitable promoter is that for the glycoprotein hormone alpha subunit which contains tandem CAMP response elements, described by Kay et al in Endocrinology 134 (2) 568–573 (1994). Another example is a construct driving the CAT enzyme which has been described by Chatterjee et al in Molecular Endocrinology 5 (1) 100–109 (1991).

However, the assay according to the present invention preferably comprises, in step (a), the use of a luciferase cDNA driven by a promoter containing CAMP response elements; and, in step (b), the use of luciferin; which means that the response measured in steps (c) and (d) is light output from the luciferinised cells. Preferably, the luciferase is Firefly luciferase, although Renilla luciferase or the like would also be suitable.

Most preferably, the reporter construct is α-luciferase, being a luciferase cDNA driven by the promoter for the glycoprotein hormone a subunit, mentioned above. For example, the plasmid pA3luc may be employed, having the glycoprotein hormone a subunit promoter introduced as described by Maxwell et al in Biotechniques 7 276–80 (1989). The α-luciferase is therefore 846 base pairs of 5' flanking sequence and 44 base pairs of exon 1 of the glycoprotein hormone a subunit promoter in the plasmid pA3luc. Alternatively, the CRE-containing sequence could be sub-cloned into a commercially-available luciferase reporter system such as the pGEM-luc vector from Promega. A further alternative is to use a plurality of plasmids, such as in the system available from Stratagene (CREB reporting system, no. 219010), which includes plasmids enabling a luciferase response to be measured following an increase in cAMP. Alternatively, inducible plasmids other than CREs could be included.

The cells may be obtained as described in the reference mentioned above by Perret et al. Alternatively, the human TSH-R could be subcloned into any eukaryotic expression vector (of which pSVL is an example) available from Stratagene, InVitrogen or the like for transfection into any eukaryotic cell or cell line. For selectivity, the more recently-developed dual vectors that incorporate the antibiotic resistance gene within the same plasmid, such as pcDNAIII (available from InVitrogen) may be used. Otherwise, a separate plasmid for selection may be employed.

Preferably, the cells used in the assay (step (a)) are those identified as from clone JP09 in the above-mentioned reference which have been stably transfected with (ie which express) in the order of $10^5$ human TSH-R per cell. More preferably, they are co-transfected with both α-luciferase cDNA and a puromycin resistance encoding plasmid such as $pSV_2Neo$ (available from Clontech) to allow selection of assay cells with puromycin. Surviving cells are then tested for luciferase activity in response to TSH. Alternatively, cells which have been transiently transfected with any of these plasmids may be employed.

Therefore, the present invention provides a bioassay comprising human TSH-R expressed in, for example, CHO cells, wherein the improvement comprises (in place of an RIA for CAMP) measuring light output from a luciferase gene driven by a promoter containing CREs. This makes the assay more rapid, enabling the complete evaluation of TSAb, from the point of serum being in contact with the cells through to obtaining data for calculation, within a single working day. Furthermore, this assay can be performed on unfractionated serum, eliminating the need for sample preparation.

Preferably, the cells would be lyophilised (freeze-dried), frozen or comprised in a gel and provided in individual containers with one container being used per assay. Alternatively, the cells could be frozen or incorporated into a gel (such as Matrigel ™), for storage.

Another co-transfection may be carried out to provide the assay with a method of correcting for the number of cells seeded in a well during use, in the case where non-lyophilised cells are to be used. Since the Renilla luciferase construct is constitutive and has different substrate requirements from Firefly luciferase, it provides such a method. The same value would be expected from every well whilst differences would reflect varying cell number. An appropriate plasmid for this transfection is the Renilla luciferase plasmid available from Promega, no. E2241. It contains the Herpes simplex virus thymidine kinase promoter upstream from Renilla luciferase, which is thus constitutively expressed.

Furthermore, when using intact rather than lyophilised cells, in order to prevent distortion of the assay by the presence of any TSH present in serum used in the cell culture medium, the serum should be charcoal-stripped at around 24 hours prior to assay.

In addition, as with the RIA, TSH responsiveness is reduced in salt-free (ie NaCl-free) conditions. To further enhance assay sensitivity, reagents such as phosphodiesterase inhibitors may be added.

The present invention therefore further provides a reporter construct comprising cDNA of both a reactant, such as an enzyme, capable of causing a measurable response when brought into contact with a corresponding substrate and a promoter containing CAMP response elements, whereby CAMP levels vary with expression of the substrate, in particular wherein the reactant is a luciferase.

Accordingly, the present invention further provides cells from a clone expressing human TSH-R (preferably,stably) transfected with a reporter construct comprising cDNA of both a reactant, such as an enzyme, capable of causing a measurable response when brought into contact with a corresponding substrate, such as a protein, and a promoter containing CRE; the clone; cDNA or mRNA expressing the (preferably stably) transfected human TSH-R; and human TSH-R (preferably stably) transfected with a reporter construct comprising cDNA of both a reactant, such as an enzyme, capable of causing a measurable response when brought into contact with a corresponding substrate and a promoter containing CRE.

Preferably, the assay according to this invention is carried out by means of a kit to enable fast and convenient results in a regular medicinal biochemistry laboratory or hospital pathology or diagnostic laboratory. The present invention therefore further provides a kit for carrying out an assay, particularly a bioluminescent assay, of the present invention, which kit comprises:

(a) cells from a clone expressing human TSH-R transfected with a reporter construct comprising cDNA of both (i) a reactant, such as an enzyme, capable of causing a measurable response when brought into contact with a corresponding substrate, such as a protein, and (ii) a promoter containing cAMP response elements whereby CAMP levels vary with expression of the reactant;

(b) a standard sample for the assay;
(c) medium for culturing and/or reconstituting the cells; and
(d) instructions for carrying out the assay according to the present invention.

The corresponding protein and reagents relating thereto, and means for carrying out the response measurements may also be provided as part of the kit. For example, the kit may further comprise:

(e) buffer for lysing the cells; and/or
(f) buffer for the reporter construct, preferably luciferase buffer; and/or
(g) corresponding substrate, preferably protein, more preferably luciferin, in buffer;
and, optionally, a luminometer.

Alternatively, for example, in the case where luciferase/luciferin are employed in the assay, a separate, commercially-available kit may be employed such as one of those available from the Promega Corporation. These commercially-available kits include no. E1483 wherein the luciferase is Firefly luciferase, and a dual-luciferase system no. E1910, which also employs Renilla luciferase.

The assay method according to the present invention and the kit therefor may be used in association with a condition or disease selected from: autoimmune thyroid disease, non-autoimmune thyroid disease, autoimmunity of non-thyroid origin and polyendocrine disease. For example, they may be used in screening patients selected from: pregnant women, those with euthyroid eye disease, and those receiving amiodarone and/or lithium. The assay method or kit according to the invention is suitable for measuring TSAb or TBAb, or for measuring autoantibodies to the TSH-R having part of its sequence modified, such as by having one or more of its amino adds replaced or otherwise modified to include tags.

The present invention will now be illustrated with reference to the following non-limiting examples:

EXAMPLE 1

Preparation of Cells for use in Luminescent Assay for TSH and TSH-R Antibodies—Use of Firefly Luciferase Chinese hamster ovary cells (CHO-K1), available from the ATCC number CCL61, were subjected to calcium phosphate co-transfection, using standard protocols (Current Protocols in Molecular Biology, 1996, John Wiley & Sons Inc. section 9.1.4), with $pSV_2Neo$ (available from Clontech) and a eukaryotic expression vector carrying the human TSH-R gene, pSVL-hTSHR (available from G. Vassart, IRIBIIN, Brussels, Belgium), as described by Perret et al (1990, ibid). The cells were selected with 400 µg/ml geneticin (G418) and cloned by limiting dilution. Clone JP09 was isolated by this method (and is also available from Prof. G. Vassart), which expresses approximately $10^5$ receptors per cell, as assessed in TSH binding experiments (described by Costagliola S, Swillens S, Niccoli P, Dumont J, Vassart G. Ludgate M in J Clin Endocrinol Metab 75 1540 et seq. (1992)).

JP09 cells were maintained at 37C in 5% carbon dioxide in air in Ham's F12 medium with 10% foetal calf serum.

Clone JP09 was co-transfected, again using the above-noted standard calcium phosphate method, with a eukaryotic expression vector carrying the puromycin resistance gene (available from, inter alia, InVitrogen, Stratagene etc.) and pA3Luc (available from V. Chatterjee, Univ. Cambridge, UK). Cells were selected in puromycin, 2.5 µg/ml and cloned by limiting dilution. Clones were tested for light output (see Example 3) in response to bovine TSH (from Sigma, T8931). Clones giving a good TSH response were tested with a panel of normal human sera, the selection criterion in this cas being a low light output of $\leq 1.5$ relative light units.

EXAMPLE 2

Preparation of Cells for use in Luminescent Assay for TSH and TSH-R Antibodies—Use of Firefly and Renilla Luciferases The method of Example 1 was followed, but after the second co-transfection involving the puromycin resistance gene, another co-transfection was carried out repeating the standard calcium phosphate method, but instead with a eukaryotic expression vector carrying the hygromycin resistance gene (available from Stratagene) and the R. luciferase plasmid E2241 (available from Promega).

EXAMPLE 3

Assay for Measurement of (i) TSH Bioactivity and (ii) Thyroid Stimulating (TSAB) or (iii) Blocking (TBAB) Antibodies Culture medium for the cells was RPMI; 10% foetal calf serum (FCS); 1% glutamine; 1% pyruvate; 2% penicillin/streptomycin (and 2.5 µg/ml puromycin, when amplifying cells for assay). 96 well plates were seeded with $5 \times 10^4$ cells prepared according to Example 1 and cultured overnight (approximately 16 hours) at 37° C. in a water-saturated incubator. They were then cultured for a second night in medium containing 10% charcoal stripped calf serum instead of FCS (available from Gibco). Basal light output was measured, in triplicate wells, in the presence of 100 µl of the medium containing 10% charcoal stripped serum. Standards (see below) and test samples were in the form of 10% patient serum to a final volume of 100 µl of the medium containing 10% charcoal stripped calf serum. Basal, standard and test incubations were for 2–3 hours as above. The final result was expressed as relative light units (RLU) obtained by the ratio of standard:basal or test:basal.

TSH bioactivity: this test is for patients having high circulating TSH levels when measured by radio-immunoassay but low circulating free T4, indicative of hypothyroidism because of defective TSH. Standards are well-characterised euthyroid and hypothyroid serum samples of increasing biological activity.

TSAb measurements are made in thyrotoxic patients. Standards are pooled normal human serum (having a light output of $\leq 1.5$ RLU), bTSH and well-characterised TSAb containing sera of increasing activity.

TBAb measurements are made in the same patients as in (i), but the assay wells also contain 1 mU/ml of bTSH. Standards are pooled normal sera +1 mU/ml bTSH and well-characterised TBAb containing sera of increasing activity.

Measurement of Light Output

Following the incubation period, supernatants were removed from the wells and the cells are washed twice in phosphate buffered saline. Light output was measured using a commercially-available kit from the Promega Corporation, no. E1483, according to the manufacturer's instructions. This involved treating the cells in lysis buffer (Promega no. E1513), adding the Firefly luciferase reagent and measuring the light output in a luminometer.

If the cells used for the assay also express Renilla luciferase constitutively (as prepared in Example 2) to give a method of standardisation of cell number/well, the Promega Dual-Luciferase system is used, no. E1910. In this case, following measurement of the Firefly luciferase as above, a reagent to quench the luminescent signal is added followed by the Renilla luciferase reagent and a second reading taken.

EXAMPLE 4

Selection and Use of Lulu1 Cells for Assay

JP09 cells were subjected, as described in Example 1, to standard calcium phosphate transfection, either with 5 µg cAMP-luciferase and 2 µg pBABE puro or with the puromycin resistance plasmid alone. cAMP-luciferase is 846 bp of 5' flanking region and 44 bp of exon 1 of the glycoprotein hormone α subunit promoter, which contains two CAMP respons elements (CREs) in tandem, linked to the firefly luciferas gen (as described by Chatterjee et al in Mol Endocrin 5 100–110 (1991)). Pools of puromycin resistant cells w re obtained following selection and tested, in 6 well plates, for light output in response to bovine TSH (as described in Example 3). Colonies were isolated using cloning rings.

(a) Selection of Lulu1

The selected clones were cultured overnight in medium with 10% charcoal-stripped calf serum (Sigma) in place of FCS, followed by 4 hours' incubation with varying concentrations of bovine TSH. Light output was measured by luciferase reporter assay (Promega) in a Berthold luminometer. Results were calculated as the ratio of light output in the presence of TSH:light output in the absence of TSH and expressed as relative light units (RLUs). Clones showing a good response to TSH were then cloned by limiting dilution and re-tested with bovine and human TSH and international TSAb standard 90/672.

(b) Determination of a Reference Range

Approximately $2\times10^4$ lulu 1 cells were seeded in 96 well plates and switched to 100 µl/well Ham's F12 containing 10% charcoal-stripped calf serum the day before the assay. 34 euthyroid sera from individuals negative for thyroglobulin and thyroperoxidase antibodies, and having no known history of thyroid disease were tested, in duplicate, by adding 10 µl directly to the wells and incubating at 37° C. for 4 hours. Cells were assayed as described in (a) above, but using a Berthold 96 well plate luminometer. Results are expressed in RLU, as the ratio between the light output in the presence of the individual serum:light output in the absence of serum. Subsequently, the 34 sera were pooled to provide a negative control.

Sera from 100 treated patients with GD, 50 negative in a commercial TBII (TSH-R) assay (TRAK, BRAHMS Diagnostica, Berlin; the cut-off was 9 units, and the functional assay sensitivity and upper limit of detection were 8 and 405 TRAK units, respectively) and 50 positive, were assayed in duplicate, by adding 10 µl serum directly to the wells. The assay was also performed on 20 Hashimoto's, 27 multinodular (8 toxic) goitre, 20 systemic lupus erythematosus and 12 rheumatoid factor positive arthritis sera. All results were calculated in RLU as in (a) above.

(c) Comparison of cAMP measured by Luminescence/RIA 44 of the GD sera described above, (35 TBII (TSH-R) positive) and the TSAb standard, were also assayed in a traditional bioassay in which CAMP released into the culture medium was measured by RIA. Lulu 1 were seeded in 96 well plates and the assay was performed in 100 µl/well NaCl-free Hank's medium, containing 2 mM IBMX and 10 µl individual GD or pooled euthyroid serum. CAMP was measured by the CAMP [$^3$H] assay system (Amersham) as described by Ludgate et al in Exp Clin Endo 100 73–4. These results are shown in the following table (Table 1), in which: ^=mean luminometer readings (n=3) with background light emission subtracted, (SEM); and *= mean (n=2) pmoles CAMP, (SEM).

TABLE 1

|  | ^RLUs | *pmole cAMP |
|---|---|---|
| blank | 98 (4) |  |
| 1 mU/ml TSH | 1293 (93) | 9.4 (0.8) |
| TSAb (90/672) 10 mlU/ml | 1245 (80) | 15.0 (1.1) |
| Forskolin $10^{-5}$M | 1651 (43) |  |
| euthyroid | 127 (5) | 2.2 (0.2) |

Detection of TSAb in Treated GD

An upper limit of <1.45 RLU was derived from the 97.5th percentile of analysis of 34 euthyroid samples (range 0.96–1.48 RLU). When the GD sera were assayed in physiological conditions, 66% of the TBII negative and 80% of the TBII positive sera produced >1.5 R.L.U. in the luminescent assay, which was obtained with only 4% of the various disease group control sera.

The intra-assay variation was 11.9%, calculated using the 100 GD sera and the inter-assay variation was 14.6% calculated from the 100 GD samples measured in two separate assays by paired analysis.

33 of the sera were positive in the luminescent assay, 27 by RIA, 7 were negative in both assays and 6 were positive by RIA but negative in the luminescent assay. Results using the three assays for TSH-R antibodies in the 100 GD sera are shown in the following table (Table 2):

TABLE 2

|  | TBII | TSAb (lumi) | TSAb (RIA) |
|---|---|---|---|
| All treated GD | 50/100 | 73/100 |  |
| TBII + ve GD | 50/50 | 40/50 |  |
| TBII – ve GD | 0/50 | 33/50 |  |
| treated GD | 35/44 | 33/44 | 27/44 |

In the conditions employed, the luminescent bioassay of this invention performed better than the traditional RIA measurement for cAMP, perhaps since the indirect measurement, via light output, amplifies the response. The behaviour of the standard exemplifies this: in the luminescent assay, the flight output was approximately 10 times that of the normal pool; while, in the RIA, it gave only a 7-fold increase.

It has also been observed that TSH responsiveness is decreased in salt-free (NaCl-free) conditions, and preliminary studies show that the luminescent assay is more sensitive for measuring TSAb but less for TSH when compared with isotonic.

What is claimed is:

1. A clone stably transfected with a gene expressing wild-type human thyrotropin receptor and a reporter construct comprising cDNA of both
   (i) a reactant capable of causing a measurable response when brought into contact with a corresponding substrate, and
   (ii) a promoter containing cAMP response elements (CREs), comprising a promoter sequence or synthetic oligonucleotide which contains the CRE consensus sequence, TGACGTCA,
   whereby reactant expression varies with the levels of cAMP; and wherein the promoter sequence or synthetic oligonucleotide is that for the glycoprotein hormone alpha subunit that contains a tandem repeat of the CRE consensus sequence, TGACGTCA.

2. The clone according to claim 1, wherein the reactant is a luciferase and/or the substrate is luciferin.

3. The cell line produced by a clone according to claim 1.

* * * * *